United States Patent
Mathias (10) Patent No.: US 8,262,639 B2
(45) Date of Patent: Sep. 11, 2012

(54) IRREVERSIBLE FLOW CONTROL CLAMP

(75) Inventor: Jean-Marie Mathias, Gesves (BE)

(73) Assignee: Fenwal, Inc., Lake Zurich, IL (US)

( * ) Notice: Subject to any disclaimer, the term of this patent is extended or adjusted under 35 U.S.C. 154(b) by 242 days.

(21) Appl. No.: 12/635,440

(22) Filed: Dec. 10, 2009

(65) Prior Publication Data

US 2010/0152681 A1 Jun. 17, 2010

Related U.S. Application Data

(63) Continuation-in-part of application No. 12/401,332, filed on Mar. 10, 2009, which is a continuation of application No. 10/501,571, filed as application No. PCT/US03/01758 on Jan. 21, 2003, now abandoned.

(60) Provisional application No. 60/353,930, filed on Jan. 31, 2002.

(51) Int. Cl.
*A61B 19/00* (2006.01)
*A61M 5/32* (2006.01)
*A61M 5/00* (2006.01)

(52) U.S. Cl. .................. 604/403; 604/250; 604/409

(58) Field of Classification Search ........ 604/4.01–6.16, 604/244, 262, 403–416, 250; 251/9, 10, 251/209
See application file for complete search history.

(56) References Cited

U.S. PATENT DOCUMENTS

| | | |
|---|---|---|
| 2,722,932 A | 11/1955 | Hickey |
| 2,908,476 A | 10/1959 | Hidding |
| 2,950,716 A | 8/1960 | Walter et al. |
| 3,127,892 A | 4/1964 | Bellamy, Jr. et al. |
| 3,942,228 A | 3/1976 | Buckman et al. |
| 4,038,726 A | 8/1977 | Takabayashi |
| 4,053,135 A | 10/1977 | Saliaris |
| 4,097,020 A | 6/1978 | Sussman |
| 4,193,174 A | 3/1980 | Stephens |
| 4,235,412 A | 11/1980 | Rath et al. |
| 4,247,076 A | 1/1981 | Larkin |
| 4,453,295 A | 6/1984 | Laszczower |
| 4,589,626 A | 5/1986 | Kurtz et al. |
| 4,643,389 A * | 2/1987 | Elson et al. ..................... 251/10 |
| 4,676,476 A | 6/1987 | Herrli |
| 4,725,269 A | 2/1988 | Danby et al. |
| 4,764,996 A | 8/1988 | Pino |
| 4,807,622 A | 2/1989 | Ohkaka et al. |
| 4,835,824 A | 6/1989 | Durham et al. |

(Continued)

FOREIGN PATENT DOCUMENTS

EP  0691 139 A1  1/1996

(Continued)

OTHER PUBLICATIONS

Extended European Search Report and Opinion for EP 09015333 dated Jun. 30, 2010.

(Continued)

*Primary Examiner* — Tatyana Zalukaeva
*Assistant Examiner* — Philip R Wiest
(74) *Attorney, Agent, or Firm* — Cook Alex Ltd.

(57) ABSTRACT

The present disclosure relates to clamps for controlling the flow of liquid through a fluid circuit. More particularly, the present disclosure relates to flow control clamps that can be substantially irreversibly secured in a closed position, thereby discouraging reopening of the flow path of the tube.

14 Claims, 6 Drawing Sheets

U.S. PATENT DOCUMENTS

| | | | |
|---|---|---|---|
| 4,857,274 A | 8/1989 | Simon | |
| 4,988,355 A | 1/1991 | Leveen et al. | |
| 5,035,399 A | 7/1991 | Rantanen-Lee | |
| 5,062,846 A | 11/1991 | Oh et al. | |
| 5,167,656 A | 12/1992 | Lynn | |
| 5,203,056 A | 4/1993 | Funk et al. | |
| 5,226,892 A | 7/1993 | Boswell | |
| 5,238,218 A | 8/1993 | Mackal | |
| 5,270,003 A | 12/1993 | Bernes et al. | |
| 5,416,954 A | 5/1995 | Sobin | |
| 5,615,965 A | 4/1997 | Saurat et al. | |
| 5,651,766 A | 7/1997 | Kingsley et al. | |
| 5,702,383 A | 12/1997 | Giesler et al. | |
| 5,817,116 A * | 10/1998 | Takahashi et al. | 606/167 |
| 5,827,306 A | 10/1998 | Yoon | |
| 5,836,619 A | 11/1998 | Shemesh et al. | |
| 5,928,166 A | 7/1999 | Shemesh et al. | |
| 6,089,527 A * | 7/2000 | Utterberg | 251/4 |
| 6,113,062 A | 9/2000 | Schnell et al. | |
| 6,123,859 A | 9/2000 | Lee et al. | |
| 6,126,618 A | 10/2000 | Bischof | |
| 6,132,407 A | 10/2000 | Genese et al. | |
| 6,161,812 A | 12/2000 | Guala et al. | |
| 6,193,675 B1 | 2/2001 | Kraus et al. | |
| 6,234,448 B1 | 5/2001 | Porat | |
| 6,238,377 B1 | 5/2001 | Liu | |
| 6,298,526 B1 | 10/2001 | Baumdicker et al. | |
| 6,328,726 B1 | 12/2001 | Ishida et al. | |
| 6,387,086 B2 | 5/2002 | Mathias et al. | |
| 6,553,632 B1 | 4/2003 | Brumpton | |
| 6,592,613 B1 | 7/2003 | Ishida | |
| 6,626,884 B1 | 9/2003 | Dillon et al. | |
| 6,638,282 B2 | 10/2003 | Ramsey | |
| 6,644,618 B1 | 11/2003 | Balbo | |
| 6,692,479 B2 | 2/2004 | Kraus et al. | |
| 6,708,931 B2 | 3/2004 | Miura | |
| 6,730,071 B1 | 5/2004 | Dassa | |
| 6,742,760 B2 | 6/2004 | Blickhan et al. | |
| 6,923,792 B2 | 8/2005 | Staid et al. | |
| 7,044,941 B2 | 5/2006 | Mathias et al. | |
| 7,087,047 B2 | 8/2006 | Kraus et al. | |
| 7,137,611 B2 | 11/2006 | Aulicino | |
| 7,384,416 B2 | 6/2008 | Goudaliez et al. | |
| 7,766,854 B2 | 8/2010 | Goudaliez et al. | |
| 2004/0106890 A1 | 6/2004 | Goudaliez et al. | |
| 2005/0038374 A1 | 2/2005 | Williams, Jr. et al. | |
| 2005/0107765 A1 | 5/2005 | Kashmiran et al. | |
| 2005/0171492 A1 | 8/2005 | Rodriguez | |
| 2005/0215975 A1 | 9/2005 | Mathias et al. | |
| 2006/0015074 A1 | 1/2006 | Lynn | |
| 2006/0129170 A1 | 6/2006 | Royce et al. | |
| 2007/0007208 A1 | 1/2007 | Brugger et al. | |
| 2007/0161978 A1 | 7/2007 | Fedenia et al. | |
| 2007/0219513 A1 | 9/2007 | Lina et al. | |
| 2007/0261214 A1 | 11/2007 | Nerbonne et al. | |
| 2008/0132875 A1 | 6/2008 | Goudaliez et al. | |

FOREIGN PATENT DOCUMENTS

| | | |
|---|---|---|
| EP | 0 799 627 A | 10/1997 |
| EP | 1 064 959 A | 1/2001 |
| EP | 1 125 596 A | 8/2001 |
| EP | 1389473 A1 | 2/2004 |
| EP | 03 703 927 | 3/2005 |
| WO | WO 93/25143 A | 12/1993 |
| WO | WO 00/77428 A2 | 12/2000 |
| WO | WO 03/063945 A1 | 8/2003 |
| WO | WO 2007/011250 A1 | 10/2007 |

OTHER PUBLICATIONS

International Search Report for PCT/US03/01758 dated Jun. 23, 2003.

Supplemental International Search Report for EP 03703927 dated Mar. 30, 2005.

* cited by examiner

ND_BAD_PAGE_OCR_10293_042

IRREVERSIBLE FLOW CONTROL CLAMP

CROSS REFERENCE TO RELATED APPLICATIONS

This application is a continuation-in-part of co-pending application Ser. No. 12/401,332 filed on Mar. 10, 2009 which is a continuation of Ser. No. 10/501,571 filed on Apr. 27, 2005, which is a national stage entry of International Application No. PCT/US03/01758, filed on Jan. 21, 2003 and designating the United States, and claims the benefit of U.S. Provisional Patent Application Ser. No. 60/353,930, filed on Jan. 31, 2002. All of the above referenced applications in their entireties are incorporated by reference herein.

BACKGROUND

A disposable plastic container and tubing set or fluid circuit is typically used for collecting blood from a donor. The disposable blood collection set includes a venipuncture needle for insertion into the arm of the donor. The needle is attached to one end of a flexible plastic tube which provides a flow path for the blood. The other end of the plastic tube is attached to one or more plastic bags or containers for collecting the withdrawn blood.

The blood collection set may also include a sampling sub-unit. The sampling sub-unit allows for collection of a sample of blood, which sample can be used for testing of the blood. Preferably, the sample is obtained prior to the "main" collection of blood. Collecting the sample prior to the main collection reduces the risk that bacteria residing on the donor's skin where the needle is inserted (i.e., in particular, the small section of detached skin commonly referred to as the "skin plug") will enter the collection container and contaminate the blood collected for transfusion. Thus, it is preferred that the blood sample, which may include the skin plug, be diverted from the main collection container.

An example of a blood collection set with such a "pre-donation" sampling sub-unit is described in U.S. Pat. Nos. 6,387,086 and 6,520,948, which are incorporated by reference herein. The collection sets described therein include a needle and a length of tubing, one end of which is attached to the needle and the other end of which is attached to one or more collection containers. The tubing set also includes an additional line which is branched from the main line at a Y-connection site in the tubing set. The branched line is attached to a sampling pouch for collecting a smaller volume of blood from which samples may be obtained.

The sampling sub-unit may further include a pre-attached holder for receiving blood sample vials or tubes. The holder is connected to the outlet port of the sampling pouch and includes a needle in the holder interior. When the blood sample vial is inserted into the holder, the needle pierces the rubber cap (septum) of the vial and blood from the sampling pouch is drawn into the vial. The blood-filled vial is removed from the holder and the procedure may be repeated with as many vials as required.

The blood collection set described above also includes flow control clamps for controlling the flow of biological fluid (e.g., blood) through the set and to the sampling pouch and/or collection container. Flow control clamps commonly used are the Roberts-type clamps, which are well known in the art. The Roberts-type clamps are placed on the tubing line leading to the blood collection container and on the tubing line leading to the sampling pouch. A Roberts-type clamp is typically made from a strip of plastic. The ends of the strip are curved toward each other to provide two "legs" which are adapted to engage each other in a snap-fit, spring relation. The body of the clamp includes a pair of apertures through which the tubing passes.

The clamp further includes a pair of projections or tube contacting members which compress the tubing when the body of the clamp is depressed, thereby restricting flow through the tube. Clamps of this type are generally described in U.S. Pat. Nos. 3,942,228, 6,089,527 and 6,113,062, all of which are incorporated herein by reference.

The clamps described in these patents also typically include means for locking the legs together and release means which, when actuated by the technician, disengages the locked legs of the flow control clamp. Disengagement of the ends decompresses the tube and permits fluid flow through the flow path. Thus, by selectively opening and closing the different flow paths (by depressing or releasing the clamps), the technician can control the flow of blood from the donor, diverting the blood to the desired container or sampling pouch, as necessary.

In certain instances, however, it may not be desirable to reopen a closed flow path. This may particularly be the case when drawing blood samples from the sampling pouch into sample vials. For example, when the sampling pouch is filled with the required or desired volume of blood (for sampling), the line from the donor to the pouch is typically closed by the Roberts-type clamp, and remains closed as the sampling vials are filled. After clamping the sampling line closed, technicians are further instructed to more permanently seal the line using metal clips or by heat-sealing the line in ways that will be known to those in the field. Sealing the sampling line substantially ensures that airborne bacteria or other contaminants that may enter the set through the sampling sub-unit do not contaminate the remainder of the set, including the needle and tube leading to the collection container. In short, the clips or heat seal provide a sterile barrier to the remainder of the set.

Unfortunately, on occasion, prior to permanently sealing the sampling line, some technicians have been known to unclamp the sampling line in order to draw additional blood into the pouch so that additional sample vials may be filled. However, by doing so, the system becomes "open" and contaminants introduced from the outside environment may enter the system. Current flow control clamps are readily and easily openable, and do not provide a disincentive to drawing additional blood into the sampling pouch. If the clamp could not be so readily released from the closed position, the technician would not have the option of reopening the line but would, hopefully, proceed with permanently sealing the line to form the sterile barrier. Accordingly, it would be desirable to provide a clamp that discourages and substantially prevents the reopening of the sampling or other blood tube line.

SUMMARY

In one aspect, the present disclosure is directed to a clamp for controlling flow through a fluid circuit. The clamp includes a flexible body having a central portion and first and second legs extending from the central portion. The legs are disposed relative to each other in a generally facing relationship and the body includes a pair of apertures for receiving flexible tubing therethrough. One of the apertures is disposed in the central portion and the other of the apertures is disposed in at least one the legs. The legs are movable from a first open spaced apart position to a second closed irreversibly locked position. First and second locking mechanisms are associated with the legs and the first locking mechanism is positioned farther from the central portion than the secondary locking mechanism.

In another aspect, the present disclosure is directed to a fluid processing set. The set includes a container adapted for receiving biological fluid from a donor, a donor access device and a tubing segment which defines a flow path that is in flow communication with the container and the access device. The set further includes a flow control clamp associated with the tubing segment. The clamp includes a flexible body having a central portion and first and second legs extending from the central portion. The legs are disposed relative to each other in a generally facing relationship and the body includes a pair of apertures for receiving the tubing segment therethrough. One of the apertures is disposed in the central portion and the other of the apertures is disposed in at least one the legs. The legs are movable from a first open spaced apart position to a second closed irreversibly locked position. First and second locking mechanisms are associated with the legs and the first locking mechanism is positioned farther from the central portion than the secondary locking mechanism. The clamp includes at least one tube contacting member carried by one of said legs for clamping the tubing segment when the legs are in the irreversibly locked position.

DETAILED DESCRIPTION

Figures 1, 2:
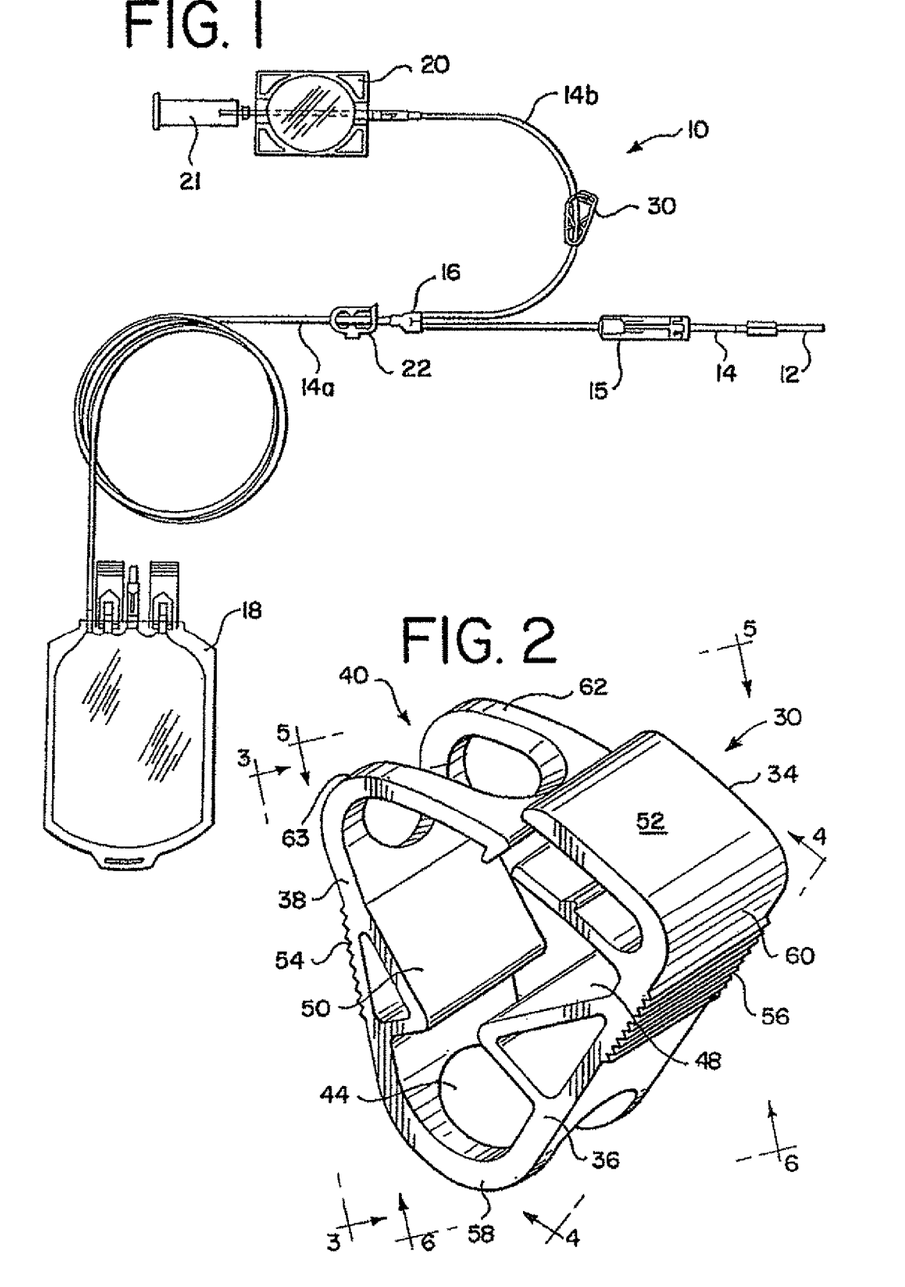
FIG. 1 is a perspective view of a blood tubing set including a flow control clamp as disclosed herein.
FIG. 2 is a perspective view of a flow control clamp as disclosed herein.

With reference to the drawings, FIG. 1 depicts a blood collection set 10 of known type that is used in the collection of blood from a donor. Tubing set 10 includes a venipuncture needle 12 and a length of tubing 14. Tubing 14 branches at for example, Y-connector 16 into tubing segment 14a and tubing segment 14b. Tubing segment 14a provides a flowpath to a collection container 18 and tubing segment 14b provides a flow path to a second container, such as, a sampling pouch 20. The sampling pouch may also include a holder 21 for receiving a blood sampling vial or tube. (Also shown is a needle protector 15 for storing the needle after use.)

In the blood tubing sets of the type shown in FIG. 1, tubing segments 14a and 14b are passed through flow control clamps 22 and 30 which may be a standard Roberts-type clamp and an irreversibly closable flow control clamp embodying the present invention. As used herein, the terms "irreversibly" closed, closable or locked means that the flow control clamp, once in the closed position, is not readily releasable from the closed position in the normal and intended mode of operation. An "irreversibly" closed, or closable or locked flow control clamp can only be released from the closed and locked position by extraordinary and unintended manipulation of the clamp, including breakage of the clamp. A flow control clamp that is "irreversibly" closed, closeable or locked restricts flow through the flow path that extends through the clamp and does not allow for flow to be re-established without extraordinary or unintended manipulation. A flow control clamp that is "irreversibly" closed or closable includes no release members such as, but not limited to, the release members described in U.S. Pat. Nos. 3,942,228, 6,089,527, 6,113,062.

Thus, for example, whereas flow control clamp 22 (e.g., a standard Roberts-type clamp) can be selectively opened and closed, as desired, clamp 30, which is the subject of the present disclosure, once closed, remains irreversibly closed, as defined above.

Turning now to FIG. 2, flow control clamp 30 of the present disclosure includes a generally curved, bent or otherwise non-linear body 34 (described in more detail below). Preferably, flow control clamp 30 may be made of any flexible, moldable, plastic material that can be steam sterilized. In addition, flow control clamp 30 and body 34 should be made of a material that is strong, yet sufficiently flexible so that the clamp can be flexed and squeezed by the technician without breaking. Examples of suitable materials are many of the known plastic materials typically used in the medical field, including, but not limited to polyoxymethylene and polypropylene. Most preferred of the above-identified materials is polyoxymethylene, such as the polyoxymethylene known as Hostaform™ available from Ticona of Frankfurt, Germany. In addition, other materials that can be sterilized by other forms of sterilization, such as gamma sterilization, may also be used. One such material is a terpolymer of acrylonitrile, butadiene and styrene (ABS).

Figure 4:
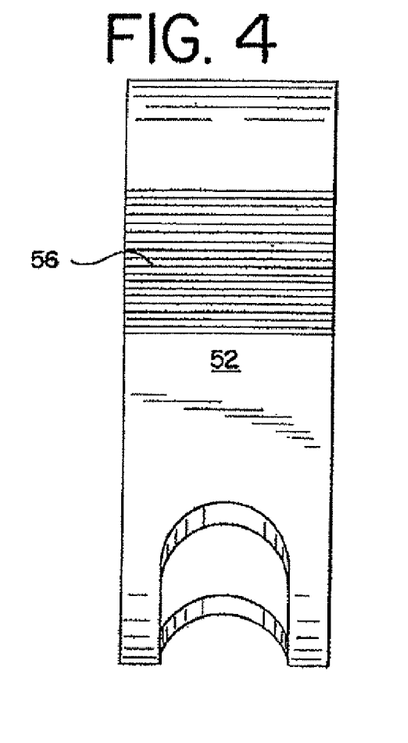
FIG. 4 is a plan view of the flow control clamp of FIG. 2 taken along lines 4-4 of FIG. 2.
Figure 5:
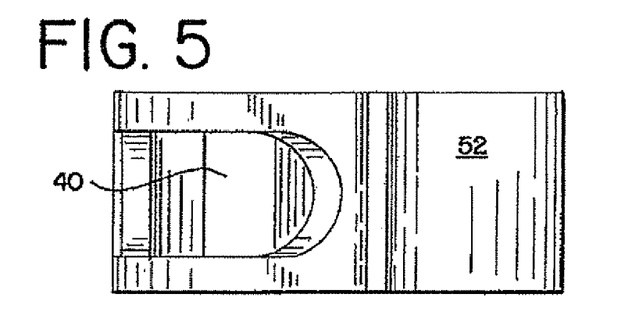
FIG. 5 is a plan view of the flow control clamp of FIG. 2 along lines 5-5.
Figure 6:
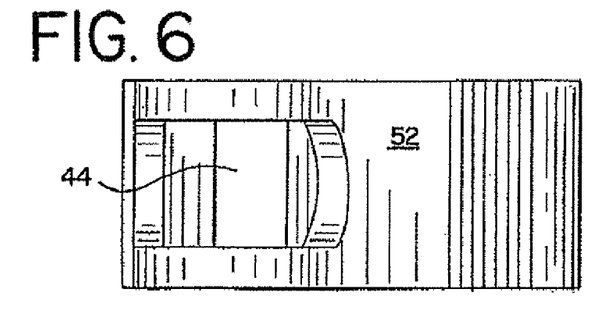
FIG. 6 is a plan view of the flow control clamp of FIG. 2 taken along lines 6-6.
Figure 7:
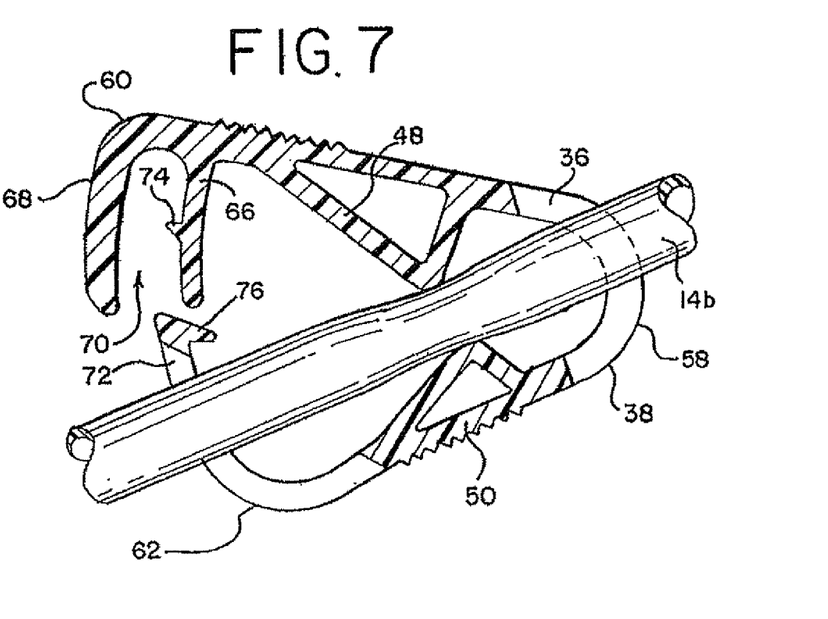
FIG. 7 is a cross-sectional, side view of the flow control clamp of FIG. 2 in the open position.
Figure 8:
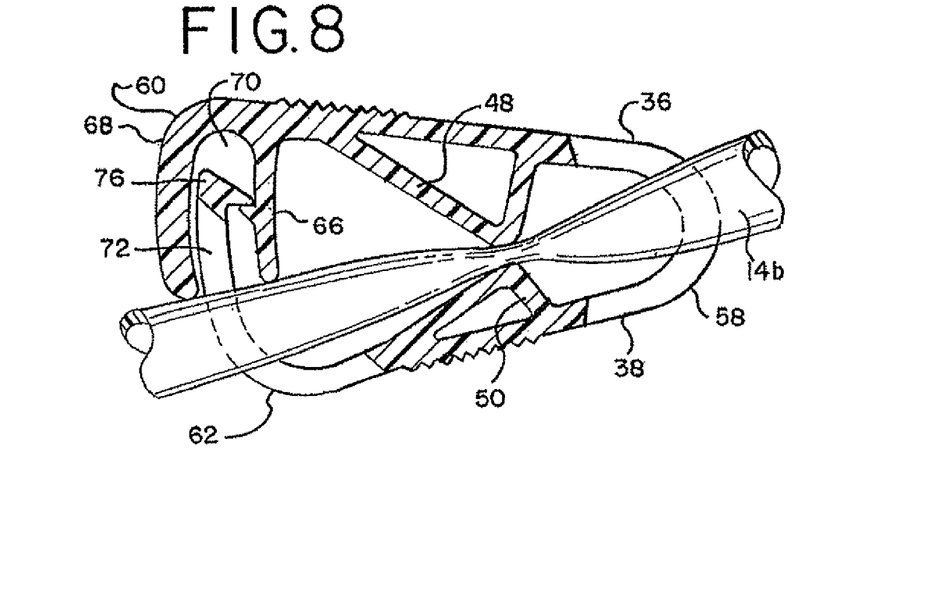
FIG. 8 is a cross-sectional, side view of the flow control clamp of FIG. 2 in the irreversibly locked position.

As further shown in FIG. 2, flow control clamp 30 includes body 34 that has a central portion 35 and two legs 36 and 38 extending therefrom. Legs 36 and 38 are disposed in a generally facing relationship relative to each other. Legs 36 and 38 are initially in a spaced apart position as shown in FIG. 4, and are movable from the first open spaced apart position toward each other to ultimately a second irreversibly closed or locked position as shown in FIG. 5.

Clamp body 34 further includes apertures 40 and 44 for receiving a length of plastic tubing therethrough. In the illustrated embodiment, aperture 44 is defined within the central portion 35 of body 30 and aperture 40 is defined in leg 38; however, it will be appreciated that the aperture may be defined in leg 40 or by a combination of the legs. As shown in FIG. 2, apertures 40 and 44 are preferably circular or oval-like and are entirely contained within body 34 of flow control clamp 30. Thus, when a length of tubing 43 is inserted through apertures 40 and 44, the rim defining the aperture completely encloses and surrounds the tubing at the point where the tubing extends through the apertures. Also, it may be preferable that apertures 40 and 44 be generally aligned with each other and not substantially offset relative to one another. This provides, among other things, for easier threading of the length of tubing 43. Alternatively, apertures need not completely surround the tube, but instead may include lateral slots, as described, for example, in U.S. Pat. No. 6,113,062. The lateral slots extend to the outer edge of the body so that during insertion of the tube, the clamp can be laterally slipped on the tube (as opposed to threading).

Flow control clamp 30 includes one or more tube contacting members 48 and 50. Tube contacting members 48 and 50 are carried by legs 36 and 38, respectively. As shown in FIG. 2, tube contacting members 48 and 50 may be teeth-like projections which compress the tubing when the clamp is closed. Alternatively, tube contacting members 48 and 50 may simply be blunt, oppositely facing surfaces. Although two oppositely facing contacting members are shown in FIG. 2 and are preferred, it will be understood that flow control clamp 30 of the present disclosure may include only one tube contacting member carried by one of the legs 36 or 38.

Figure 3:
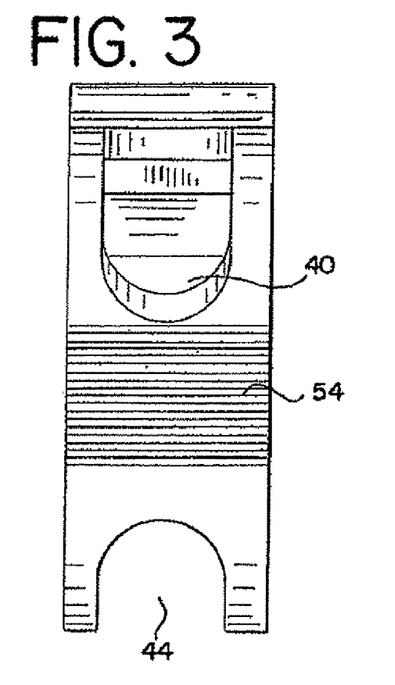
FIG. 3 is a plan view of the flow control clamp of FIG. 2 taken along lines 3-3 of FIG. 2.

The outer surface 52 of flow control clamp 30 is generally flat and smooth. However, outer surface 52 may include portions that are roughened or textured to provide some friction when contacted by the fingertips of the technician during operation. As shown in FIGS. 3-5, outer surface 52 of body 34 includes ribbed portions 54 and 56, which provide such a frictional surface for contacting by the fingers of the technician during closure and compression of flow control clamp 30.

As best shown in FIGS. 4 and 5, flow control clamp 30 is substantially free of any sharp corners or edges. For example, bends 58, 60 and 62 in body 34 are not abrupt, sharp corners, but are gradually curved and rounded. In addition, edges 63 of body 34 are preferably rounded or beveled. A flow control clamp 30 that is substantially free of sharp corners and edges and is more rounded or beveled, like the flow control clamp shown in FIGS. 4 and 5, ensures that the flow control clamp will not puncture the packaging of blood processing sets, thereby maintaining sterility of the packaged set.

As discussed generally above, where the blood processing set includes a sampling pouch of the type shown in FIG. 1, it may be desirable to provide a flow control clamp 30 that provides an additional level of sterility maintenance by discouraging and/or perhaps even preventing the technician from reopening a previously closed clamp. This way, the sterility of the remainder of the blood processing set will be maintained and will not be compromised by bacteria from the outside environment, or the collected sample in sample pouch 20 will not be diluted by, for example, anticoagulant in the fluid set.

Accordingly, flow control clamp 30 includes a locking mechanism, and more particularly, legs 36 and 38 include surfaces that are disposed for irreversibly securing together legs 36 and 38 when the legs of flow control clamp 30 are moved from a first spaced-apart position to the second closed position, as shown in FIGS. 4 and 5 respectively.

Many different ways for securing legs 36 and 38 together to prevent easy reopening by the technician are contemplated by the present disclosure. For example, flow control clamp 30 may include means on the leg surfaces for interlocking legs 36 and 38. Specifically, as shown in FIGS. 4 and 5, leg 36 of flow control clamp 30 may include a pair of spaced-apart walls 66 and 68 that depend or otherwise extend from leg 36 at a distal end of the clamp. Spaced-apart walls 66 and 68 define a slot 70 for receiving an extension 72 carried by leg 38. One of the spaced-apart walls 66 or 68 may further include a lip 74 that projects into slot 70, while the extension 72 includes a hook 76 that projects toward the wall 66.

As the legs 36 and 38 are moved from the first open spaced-apart position, as generally depicted in FIG. 4, to the second closed irreversibly locked position, tube contacting members 48 and 50 compress the tube 43, thereby restricting flow therethrough. As flow control clamp 30 is compressed further, extension 72 is outwardly displaced by wall 66 and enters slot 70. As hook 76 contacts lip 74, extension 72 is again outwardly displaced until it clears lip 74. Once clear of lip 74, extension 72 snaps forward toward wall 66, and hook 76 engages lip 74 to effectively close and lock flow control clamp 30.

Wall 68 prevents release or further outward displacement of extension 72 from the closed position, thereby resulting in an "irreversibly closed" flow control clamp 30. As shown in FIG. 5, wall 68 is a thicker and a less flexible wall than, for example, wall 66, thereby providing more strength to wall 68 and making it even more difficult to release extension 72. As will be appreciated by those in the field, flow control clamp 30 does not include any tabs or other means for readily releasing extension 72. Thus, flow control clamp 30 remains in the second closed position. In addition, clamp 30 lacks any easy-to-grasp surface or member that can be used to pry open the clamp when it is in the second closed position. For example, clamps that have tabs or outwardly extending members or surfaces may be more susceptible to re-opening by being grasped by a user or accidentally caught on an object and used as a lever arm to pry open the clamp. In contrast, the interengaging member of the locking mechanism (e.g., walls 66, 68 and extension 72) as described above are contoured relative to each other and are in sufficiently close association so as to be devoid of any easy-to-grasp surface or member to allow grasping or other manipulation that could result in relatively easy re-opening of the clamp. Accordingly, the compact and contained body of clamp 30 with the locking mechanism protected at the distal end assists in preventing inadvertent or even intentional opening of the clamp once in the second closed position.

Figures 9, 10:
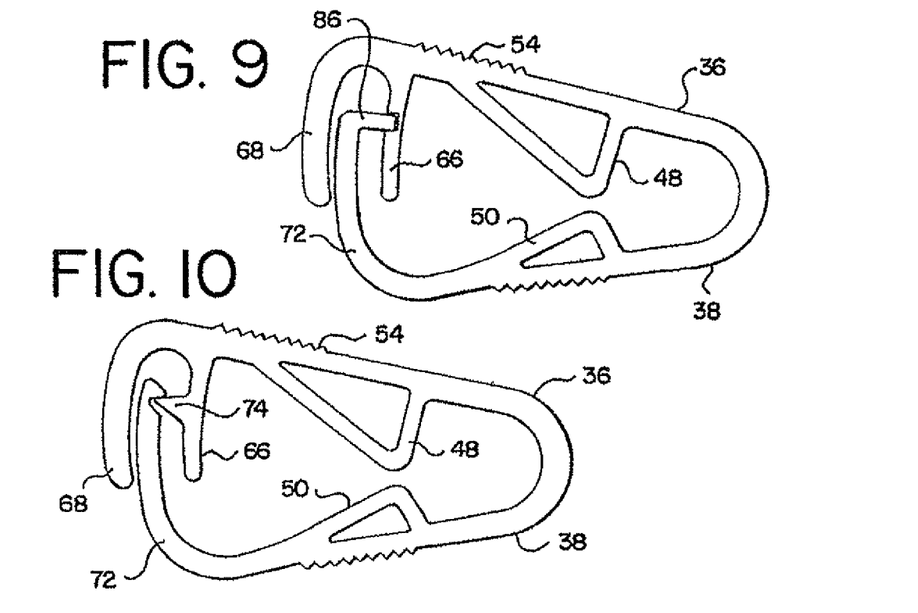
FIG. 9 is a side view of an alternative embodiment of the flow control clamp as disclosed herein.
FIG. 10 is a side view of another alternative embodiment of the flow control clamp as disclosed herein.

FIGS. 9-12 include additional means for securing legs 36 and 38 in an "irreversibly closed" position. For example, as shown in FIG. 9, extension 72 may include a peg, and wall 66 includes a mating notch 84 for receiving peg 86 of extension 72 at a distal end of clamp 30. Extension 72 enters slot 70 in the manner generally described above, until peg 86 snaps into notch 84. Wall 68 again prevents outward movement of extension 72, thereby retaining flow control clamp 30 in an "irreversibly closed" position.

Figures 11, 12:
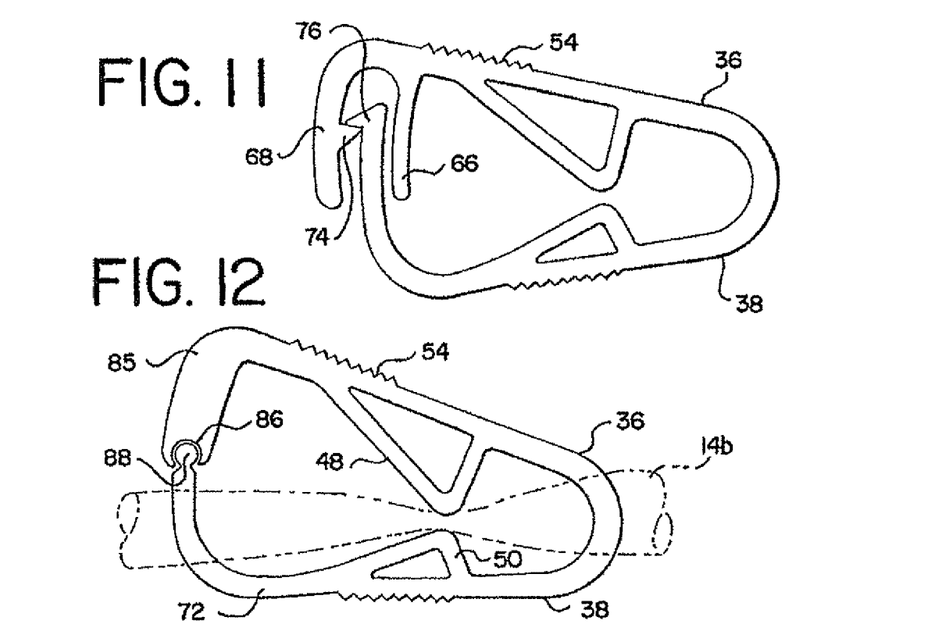
FIG. 11 is a side view of another alternative embodiment of the flow control clamp as disclosed herein.
FIG. 12 is a side view of still another alternative embodiment of the flow control clamp as disclosed herein.

FIG. 10 is an alternative embodiment where extension 72 includes a notch for receiving lip 74 of wall 66. In FIG. 11, lip 74 is located on wall 68 and is engaged by hook 76, as previously described.

FIG. 12 shows yet another alternative embodiment of the flow control clamp 30 of the present disclosure wherein leg 36 includes a single wall 85 projecting toward the interior (i.e., toward leg 38) of the flow control clamp 30. Leg 38 includes an extension, likewise projecting toward the interior (i.e., and toward leg 36) of the flow control clamp 30. In order to secure legs 36 and 38 in the "irreversibly closed" position, one of the legs may include a socket 86, and the other of the legs may include a ball 88 for insertion into socket 86 at a distal end of clamp 30. This way, as in the previous embodiments, flow control clamp 30 may be closed or locked in the "irreversibly closed" position.

FIGS. 13-17 illustrate a further alternative embodiment of flow control clamp 30 which includes among other things, a second locking mechanism that can be used in combination with the first locking mechanism as described above. The flow control clamp of FIGS. 13-17 is similar to the flow control clamp of FIGS. 1-12 and similar or identical elements will be referred to with identical reference numerals.

Figure 13:
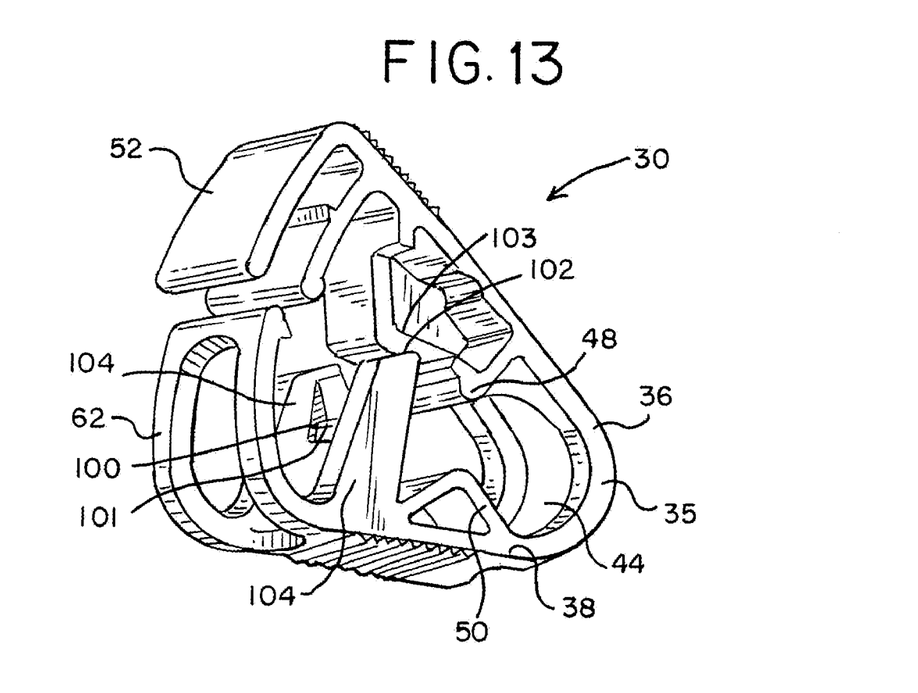
FIG. 13 is a perspective view of a flow control clamp including first and second locking mechanisms as disclosed herein.
Figure 17:
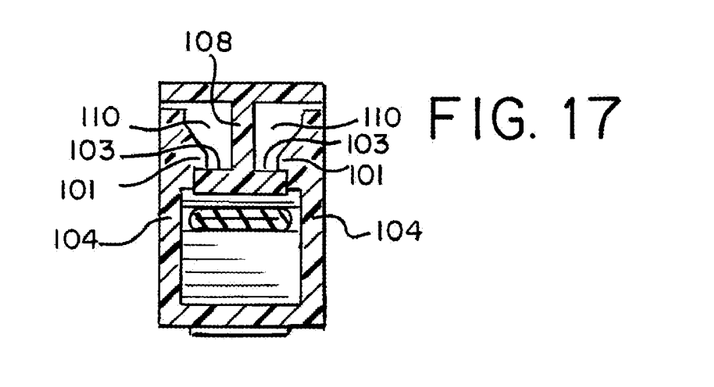
FIG. 17 is a cross-sectional, end view of the flow control clamp of FIG. 16 taken along line 16-16.

As in the embodiment described above, the clamp of the embodiment illustrated in FIGS. 13-17 includes a central portion 35 and pair of inwardly movable and facing legs 36 and 38. Similarly, clamp 30 of FIGS. 13-17 includes one or more tube contacting members 48 and 50. The illustrated embodiment also preferably includes lateral and preferably parallel arms 104 that extend from the sides of leg 38 as best seen in FIGS. 13 and 17. Lateral arms 104 may act as a guide for threading the tubing 43 through apertures 40 and 44 of the clamp and help maintain (e.g., center) the tubing within the clamp body and more specifically, between contacting members 48 and 50 (see FIG. 14). In addition, arms 104 may prevent distortion of the clamp when in the closed position. It will be appreciated that arms 104 need not extend from the outermost surface of leg 38; however, the arms should be spaced sufficiently apart such that tube 43 can freely pass between the arms without arms 104 substantially pressing against tubing 43 so as to, for example, restrict fluid flow through the tube. Leg 36 may further include a groove or cutout 112 for receiving or otherwise accommodating distal end tip 105 of one or both lateral arms 104. As will be discussed in more detail below, arms 104 may also carry one or more locking mechanisms. In an alternative embodiment, clamps provided in accordance with the present disclosure may include a "first" locking mechanism and lateral arms 104 without a locking mechanism associated with the arms (or without a second locking mechanism whatsoever) although a clamp with first and second locking mechanisms as described below is preferred.

As noted above, clamp 30 of FIGS. 13-17, includes a first locking mechanism as described above in connection with FIGS. 1-12. That is clamp 30 may include walls 66 and 68 depending from one of legs 36 and 38 to define a slot 70. The first locking mechanism of clamp 30 may include the interengaging extension 72 and hook 76 arrangements of FIG. 2, 7-8 or 11, or alternatively, the peg 86 and notch 84 arrangement of FIG. 9, the notch and lip arrangement of FIG. 10, the ball 88 and socket 86 arrangement of FIG. 12 or any other comparable mechanism for engaging one of legs 36 or 38 with the other of legs 36 or 38. As described in connection with the clamp of FIGS. 1-12, this compact clamp arrangement assists in preventing inadvertent or even intentional opening of the clamp once in the second closed position.

Figure 14:
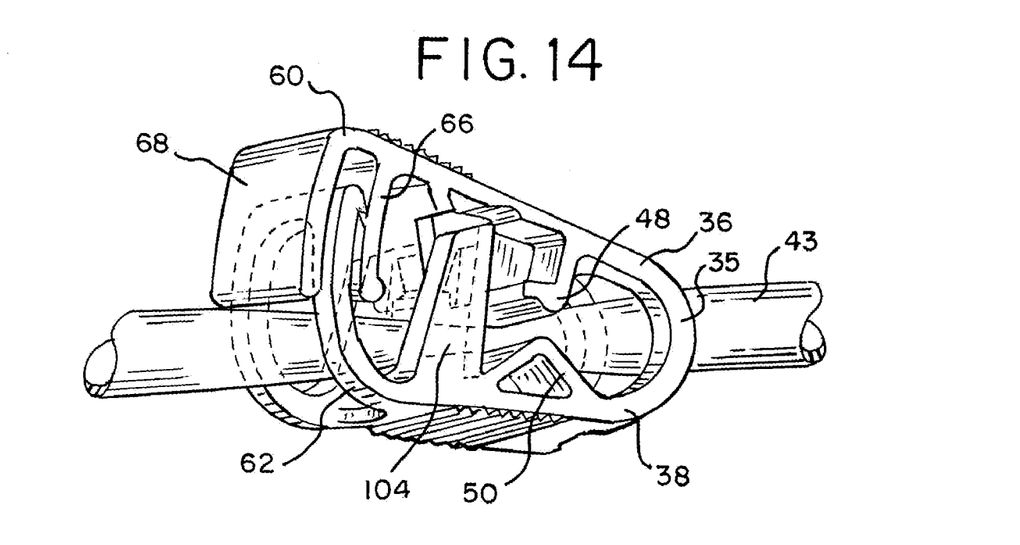
FIG. 14 is a perspective view of the flow control clamp of FIG. 13 with a flexible tube extending therethrough.
Figure 15:
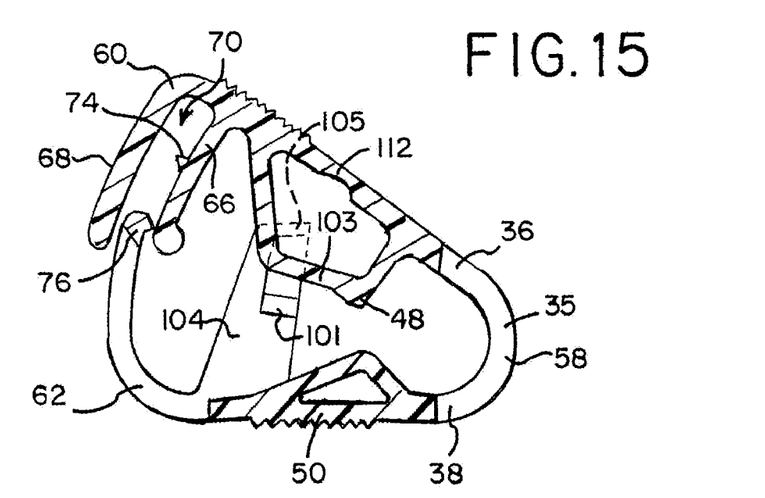
FIG. 15 is a cross-sectional, side view of the flow control clamp of FIG. 13 in the open position.
Figure 16:
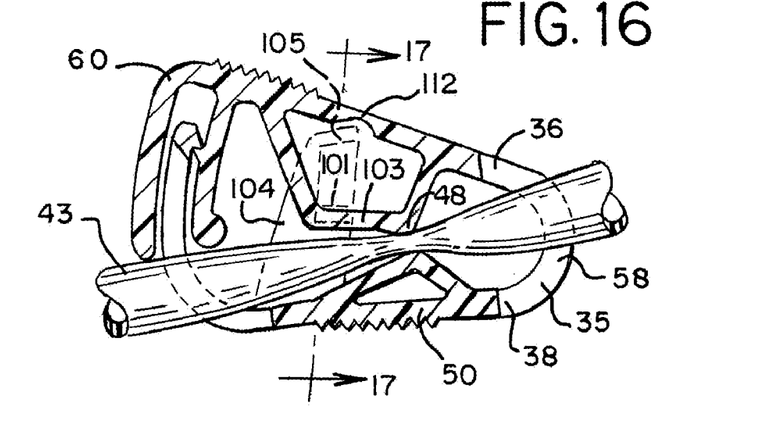
FIG. 16 is a cross-sectional, side view of the flow control clamp of FIG. 15 in the irreversibly locked position.

In addition to such first locking mechanism, clamp 30 may include a second locking mechanism that is spaced from the first locking mechanism. For example, in one embodiment a second locking mechanism may be positioned closer to central portion 35 than the first locking mechanism. For example, whereas first-locking mechanism(s) are generally located at a distal end of clamp 30, second locking mechanism is preferably spaced from the first locking mechanism. More preferably, the second locking mechanism is proximally located relative to the first locking mechanism and distally positioned relative to central portion 35. Thus, in a preferred embodiment, second locking mechanism is positioned between the first locking mechanism and central portion 35. The second locking mechanism may be positioned on either side of the contacting members (e.g., distal or proximal to contacting members). In one embodiment, second locking mechanism may include interengaging structures that are disposed on or otherwise associated with legs 36 and 38 when the legs of flow control clamp 30 are moved from a first spaced-apart position to the second irreversibly closed position, as shown in FIGS. 13 and 14 respectively.

More specifically, in an embodiment, the second locking mechanism includes first engaging member 100 associated with leg 38 and a second engaging member 102 associated with leg 36. First engaging member 100 preferably includes catch 101 and second engaging member 102 preferably includes ledge 103. As best seen in FIG. 17, ledge 103 extends laterally from central support member 108 that depends from leg 36. As flow control clamp 30 is moved from the first open position to the second closed position, catch 101 is outwardly displaced until it clears ledge 103. Once clear of ledge 103, catch 101 engages the top of ledge 103 to assist (first locking mechanism described above) in locking flow control clamp 30 in its second irreversibly closed position. The interaction between catch 101 and ledge 103 is best illustrated in FIG. 17. It is appreciated that one skilled in the art would recognize other structures that may be used on the engaging members to lock the legs together in the second position, for example, a ball and socket.

As shown in FIGS. 13-17, catch 101 is more particularly positioned on (parallel) lateral arms 104 that extend from opposite sides of leg 38. In the illustrated embodiment, the arms are formed such that as clamp 30 is moved from the first open position to the second closed position, the end tip 105 of the arms fit into a recess 110 formed by ledge 103 and support 108 (see FIG. 17). This allows leg 36 to act as a stop and limit the travel of arms 104. Alternatively, it will be appreciated that only one arm and catch may be provided in the flow control clamp 30 of FIGS. 13-17. It will be appreciated that the outer sides 120 of lateral arms 104 do not extend beyond the edges of legs 36 and 38, as best shown in FIG. 17. This, likewise provides clamp 30 with a compact and contained body that has no easy-to-grasp outwardly extending members or surfaces that would allow one to grasp and pry open clamp 20.

Ledge 103 on leg 36 may be integral with contacting member 48; however, it will also be appreciated that ledge 103 may be separate from contacting member 48. In addition, it will be understood that arms 104 may be integral with contacting member 50 and that positioning catch 101 and ledge 103 can be reversed such that ledge 103 is associated with leg 38 and catch 101 is associated with leg 36.

Regardless of the relative location of the interengaging elements of the second locking mechanism, a clamp having both first and second locking mechanisms spaced apart from each other and relatively spaced from central portion 35 provides more secure clamping. The dual locking mechanism of a clamp described above and as shown in FIGS. 13-17 would make it more difficult to re-open the clamp inadvertently or even intentionally. In other words, spacing the first and second locking mechanisms away from each other, i.e., provides engagement of legs 36 and 38 at two distinct locations. In addition, spacing the first and second locking mechanisms away from each other may allow for sequential engagement i.e., engagement of one of the locking mechanism followed by engagement of the other of the locking mechanism. The sequential engagement can be accompanied by audible "clicks" whereby a first audible "click" followed by a second audible "click" thereby providing assurance to the user that the clamp is locked in the "irreversibly closed" position. Finally, providing two separate locking mechanisms allows for a back-up locking mechanism in the event one of the two locking mechanisms fails.

It will be appreciated that the description set forth above has been offered for illustrative purposes only. Other embodiments and other modifications to the flow control clamp shown and described above will be readily apparent to one skilled in the art and may also be included within the scope of the present disclosure. The above description is not intended to limit the scope of the invention of this application, which is as defined in the claims below.

What is claimed is:

1. A flow control clamp comprising:
a flexible body comprising a central portion and a distal end, first and second legs extending from said central portion, said legs disposed relative to each other in a general facing relationship;
said body including a pair of apertures for receiving flexible tubing therethrough wherein one of said apertures is disposed in said central portion and the other of said apertures is disposed in at least one of said legs;
wherein said legs are movable from a first open spaced apart position to a second closed irreversibly locked position;
a first and second locking mechanisms associated with each of said first and second legs, wherein said first locking mechanism is located at said distal end and said second locking mechanism is located between said first locking mechanism and said central portion.

2. The flow control clamp of claim 1 wherein said locking mechanisms comprise interengaging locking structures on each of said legs.

3. The flow control clamp of claim 2 wherein said interengaging locking structures of said first locking mechanism comprises a pair of spaced apart walls defining a slot on said first leg, and said second leg including an extension, whereby movement of said legs from said spaced apart position to said closed position introduces said extension into said slot.

4. The flow control clamp of claim 3 wherein one of said spaced-apart walls is more rigid than said other of said spaced-apart walls.

5. The flow control clamp of claim 2 wherein said interengaging locking structures of said second locking mechanism comprises one of said legs having a ledge and said other leg having a catch for engaging said ledge in said closed position.

6. The flow control clamp of claim 2 wherein said interengaging locking structures of said second locking mechanism comprises a first engaging member extending from one of said legs and a second engaging member extending from said other leg.

7. The flow control clamp of claim 6 wherein said first engaging member comprises a catch disposed thereon and said second projection comprises a ledge for engaging said catch in said closed position.

8. The flow control clamp of claim 7 wherein the first engaging member includes at least one arm or a pair of arms extending from one of said legs.

9. The flow control clamp of claim 6 wherein one of said engaging members comprises a contacting member for compressing a tube when said legs are in the closed position.

10. The flow control clamp of claim 1 wherein said apertures are completely enclosed.

11. The flow control clamp of claim 1 further comprising at least one tube contacting member carried by one of said legs for compressing a tube when said legs are in the closed position.

12. The flow control clamp of claim 11 further comprising a tube contacting member carried by said other of said legs for compressing said tube between said contacting members when said legs are in the closed position.

13. A fluid processing set comprising:
a container adapted for receiving biological fluid from a donor;
a donor access device;
a tubing segment defining a flow path that is in flow communication with said container and said access device;
a flow control clamp associated with said tubing segment, said clamp comprising;
a flexible body comprising a central portion and a distal end, first and second legs extending from said central portion, said legs disposed relative to each other in a general facing relationship and are movable from a first open spaced apart position to a second closed irreversibly locked position;
said body including a pair of apertures for receiving said tubing segment therethrough wherein one of said apertures is disposed in said central portion and the other of said apertures is disposed in at least one of said legs;
a first and second locking mechanisms associated with each of said first and second legs, wherein said first locking mechanism is positioned at said distal end and said second locking mechanism is positioned between said first locking mechanism and said central portion;
at least one tube contacting member carried by one of said legs for clamping said tubing segment when said legs are in the irreversibly locked position.

14. The fluid processing set of claim 12 further comprising:
a second container for receiving biological fluid from said donor, and
a second tubing segment defining a flow path between said second container and said access device.

* * * * *